(12) United States Patent
Dierker

(10) Patent No.: US 8,461,407 B2
(45) Date of Patent: Jun. 11, 2013

(54) METHOD FOR DEHYDRATING FATTY ALCOHOLS

(75) Inventor: Markus Dierker, Duesseldorf (DE)

(73) Assignee: Cognis IP Management GmbH, Duesseldorf ( * ) Notice: Subject to any disclaimer, the term of this patent is extended or adjusted under 35 U.S.C. 154(b) by 524 days.

(21) Appl. No.: 11/886,191

(22) PCT Filed: Mar. 7, 2006

(86) PCT No.: PCT/EP2006/002062
§ 371 (c)(1),
(2), (4) Date: Apr. 10, 2008

(87) PCT Pub. No.: WO2006/097222
PCT Pub. Date: Sep. 21, 2006

(65) Prior Publication Data
US 2008/0287722 A1 Nov. 20, 2008

(30) Foreign Application Priority Data

Mar. 16, 2005 (DE) .......................... 10 2005 012 049

(51) Int. Cl.
*C07C 1/24* (2006.01)
(52) U.S. Cl.
USPC .......................................... 585/639; 585/324
(58) Field of Classification Search
USPC .............. 585/324, 328, 357, 437, 469, 638, 585/639, 640, 649; 502/170, 355; 260/682
See application file for complete search history.

(56) References Cited

U.S. PATENT DOCUMENTS

| | | | | |
|---|---|---|---|---|
| 2,957,034 A | * | 10/1960 | Eschard | 585/639 |
| 4,049,736 A | * | 9/1977 | Lamson et al. | 585/437 |
| 4,127,595 A | * | 11/1978 | Matsuura et al. | 552/286 |
| 4,155,945 A | * | 5/1979 | Levine | 585/639 |
| 4,165,343 A | | 8/1979 | Levine et al. | |
| 4,207,424 A | * | 6/1980 | Winnick | 585/357 |
| 4,847,223 A | | 7/1989 | Van Mao et al. | |
| 4,873,392 A | | 10/1989 | Le Van Mao | |
| 5,659,102 A | | 8/1997 | Triantafillou et al. | |
| 2007/0081959 A1 | | 4/2007 | Schmid et al. | |

FOREIGN PATENT DOCUMENTS

| | | |
|---|---|---|
| DE | 39 11 004 A1 | 10/1990 |
| DE | 195 11 668 A1 | 10/1996 |
| DE | 103 17 781 A1 | 11/2004 |
| DE | 103 24 508 A1 | 12/2004 |
| EP | 1 333 017 A2 | 8/2003 |
| GB | 2 181 070 A | 4/1987 |
| JP | 10231258 | 9/1998 |
| WO | WO 97/03932 A1 | 2/1997 |

OTHER PUBLICATIONS

Vollhardt, K. Peter C. et al., "Organic Chemistry Structure and Function", *W. H. Freeman and Company* Chapter 8 Hydroxy Functional Group—Alcohols 2003, 6 pgs.

* cited by examiner

*Primary Examiner* — Thuan D Dang
(74) *Attorney, Agent, or Firm* — Servilla Whitney LLC

(57) ABSTRACT

A process for the production of hydrocarbons by dehydrating primary alcohols with a dehydration catalyst of trifluoromethansulfonic acid is disclosed. The hydrocarbons so produced have fewer undesired secondary reactions. Accordingly, cosmetic and cleaning compositions incorporating the hydrocarbons produced by way of the process are also disclosed.

9 Claims, No Drawings

METHOD FOR DEHYDRATING FATTY ALCOHOLS

CROSS-REFERENCE TO RELATED APPLICATIONS

This application is a national phase filing under 35 U.S.C. Section 371 and claims priority of International Application No. PCT/EP2006/002062 filed Mar. 7, 2006, which designated the United States of America and which claims priority of German Application No. 102005012049.0 filed Mar. 16, 2005, the entire disclosures of which are incorporated herein by reference.

FIELD OF THE INVENTION

This invention relates to a process for the production of hydrocarbons by dehydration of primary fatty alcohols.

BACKGROUND OF THE INVENTION

The use of hydrocarbons in cosmetic compositions has been known for some time. For example, mineral oils and paraffin oils are used as inert oil components. They have the disadvantage that, from the sensory perspective, they leave the skin with a "heavy" feeling and spread poorly.

Many processes for the production of hydrocarbons start out from short-chain olefins which are oligomerized. Methyl-branched paraffins and their production from Guerbet alcohols in the presence of alkylsulfonic acid catalysts are disclosed, for example, in DE 3911004. The use of product mixtures of various hydrocarbons with improved spreadability, which can be obtained, for example, by the processes described in DE 103 17 781 or DE 103 24 508, is also known. Such mixtures are difficult to characterize and contain a number of different individual components with higher oligomers. Several different processes for dehydrating alcohols have been known for some time and are well-known in the art (cf. Organikum). However, many of these processes often only operate at very high temperatures (for example GB 2181070) or with comparatively unusual and expensive catalysts, such as niobic or tantalic acid (WO 97/03932).

BRIEF SUMMARY OF THE INVENTION

Accordingly, the problem addressed by the present invention was to provide a process for the production of hydrocarbons which could be carried out under moderate conditions and in which fewer secondary reactions, such as pyrolysis or etherification, would occur. It has surprisingly been found that the stated problem can be solved by the use of trifluoromethanesulfonic acid as catalyst.

The present invention provides a process for the production of hydrocarbons, which process comprises dehydrating a primary alcohol with a dehydration catalyst, wherein the catalyst is trifluoromethanesulfonic acid.

The hydrocarbons produced by way of the process of the present invention possess fewer secondary reactions, such as pyrolysis and etherification.

Accordingly, another aspect of the invention is the incorporation of the hydrocarbons produced by the way of the process of the invention into cosmetic and cleaning compositions.

DETAILED DESCRIPTION OF THE INVENTION

The present invention relates to a process for the production of hydrocarbons by dehydration of primary alcohols, characterized in that trifluoromethanesulfonic acid is used as the dehydration catalyst. Suitable primary alcohols are, for example, hexanol, heptanol, octanol, nonanol, decanol, undecanol, undecenol, dodecanol, tridecanol, tetradecanol, pentadecanol, hexadecanol, heptadecanol, octadecanol, octadecenol, nonadecanol, eicosanol, eicosenol, heneicosanol, docosanol and docosenol. The technical mixtures of primary alcohols obtainable from natural fats and oils by standard oleochemical methods may also be used in accordance with the invention. Such alcohols include caproic, oenanthic, caprylic, pelargonic, capric, lauryl, myristyl, cetyl, stearyl, arachidyl, behenyl, oleyl, elaidyl, linoleyl, gadoleyl, arachidonic, erucic and brassidyl alcohol.

Preferred primary alcohols are linear or branched, saturated or unsaturated C6-C30 alcohols. Primary C6-C18 alcohols, preferably C10-C14 alcohols, are preferably used. With C10-C14 alcohols, the reaction gives particularly good yields. In a preferred variant of the process, the alcohols are selected from branched C7-C13 alcohols. Such alcohols include Guerbet alcohols, such as 2-ethylhexanol and, in particular, the Exxal® alcohols marketed by Exxon, such as for example isoheptanol (Exxal® 7), iso-octanol (Exxal® Bn), isononanol (Exxal® 9), isodecanol (Exxal® 10), isoundecanol (Exxal® 11), isotridecanol (Exxal®) 13). Besides 2-ethylhexanol, Guerbet alcohols suitable for use in accordance with the invention include 2-propylheptanol, 2-butyloctanol and 2-hexyldecanol.

The dehydration process according to the invention is generally carried out at temperatures in the range from 190 to 260° C., preferably at temperatures in the range from 200 to 250° C. and, more particularly, at temperatures in the range from 220 to 250° C. In another embodiment of the process according to the invention, the dehydration can be carried out under reduced pressure. In this way, the reaction temperature can be further reduced so that fewer secondary reactions occur. This is a particular advantage with relatively long-chain alcohols. According to the invention, it can also be of advantage to carry out the reaction in an inert gas, such as nitrogen or argon for example.

In a preferred embodiment of the invention, the catalyst is used in a quantity of 0.5 to 3% by weight, based on the weight of alcohol, for the dehydration.

Commercial Applications

The hydrocarbons produced by the process according to the invention may be used for a variety of applications, for example in cosmetic compositions, in furniture polishes, in textile treatment preparations, etc. The relatively long-chain C10-C30 hydrocarbons, more particularly the C10-C22 hydrocarbons, are particularly suitable for the production of cosmetic body care and cleaning compositions and may be used in creams, lotions, sprayable emulsions, products for eliminating body odor, foam and shower baths, hair shampoos and care rinses.

The following Examples are illustrative of the present invention and are not intended in any manner whatsoever as limiting of the scope of the invention.

EXAMPLES

General Reaction Procedure

The alcohol was introduced with the catalyst (0.5-3%) into a distillation apparatus and heated for several hours to 240° C. Educt or product distilled off was returned to the reaction vessel via a water separator. The organic phase of the distillate obtained was dried over sodium sulfate and the product was isolated by filtration. The yield was typically >80% of the required olefin.

Example 1

Dodecene 600.0 g Lorol® C12 (dodecanol from Cognis Deutschland GmbH & Co. KG) and 18.0 g trifluoromethanesulfonic acid (25% by weight in water) were introduced into a distillation apparatus and heated for 4 h to 240° C. The organic phase of the distillate obtained (476.0 g) was dried over sodium sulfate and the product was isolated by filtration. The product contained 93.3% dodecene, 4.6% dodecanol and 1.1% didodecyl ether (GC analysis).

Example 2

Isododecane 300.0 g Lial® 123 (isododecanol from Sasol) and 18.0 g trifluoromethanesulfonic acid (50% by weight in water) were introduced into a distillation apparatus and heated for 1.5 h to 240° C. The organic phase of the distillate obtained (171.9 g) was dried over sodium sulfate and the product was isolated by filtration). The product then contained 91.5% isododecene, 7.5% Lial® 123 and 1.0% didodecyl ether (GC analysis).

Example 3

Isotridecene 1200.0 g Exxal® 13 (isotridecanol from Exxon Mobile) and 12.0 g trifluoromethanesulfonic acid (25% by weight in water) were introduced into a distillation apparatus and heated for 5 h to 240° C. The organic phase of the distillate obtained (994.6 g) was dried over sodium sulfate and the product was isolated by filtration. The product contained 94.0% isotridecene and 6.0% isotridecanol (GC analysis). IV (Kaufmann)=194, IV (Wijs)=241, OHV=22.5.

Example 4

Tetradecene 600.0 g Lorol® C14 (tetradecanol) and 12.0 g trifluoromethanesulfonic acid (25% by weight in water) were introduced into a distillation apparatus and heated for 5 h to 240° C. The organic phase of the distillate obtained (308.0 g) was dried over sodium sulfate and the product was isolated by filtration. The product then contained 84.3% tetradecene, 10.8% tetradecanol and 4.8% ditetradecyl ether (GC analysis).

What is claimed is:

1. A process for the production of hydrocarbons, which process comprises the step of dehydrating a primary alcohol comprising a linear or branched, saturated or unsaturated C6-C30 alcohol in the presence of 0.5% to 3% by weight, based on the primary alcohol, of a dehydration catalyst comprising trifluoromethanesulfonic acid, at a temperature in the range of 220 to 250° C., to provide a product which consists essentially of olefins.

2. The process of claim 1 wherein the primary alcohol comprises a C6-C18 alcohol.

3. The process of claim 2 wherein the primary alcohol comprises a C10-C14 alcohol.

4. The process of claim 2 wherein the primary alcohol comprises a branched C7-C13 alcohol.

5. The process of claim 1 wherein dehydration is carried out under reduced pressure.

6. The process of claim 1, wherein said temperature is 240° C.

7. The process of claim 5, wherein said product contains >80% olefins.

8. The process of claim 1, wherein the reaction mixture consists essentially of the primary alcohol and the dehydration catalyst comprising trifluoromethanesulfonic acid.

9. The process of claim 1, wherein the product is effective for cosmetic body care and cleaning compositions.

* * * * *

UNITED STATES PATENT AND TRADEMARK OFFICE
CERTIFICATE OF CORRECTION

PATENT NO. : 8,461,407 B2  
APPLICATION NO. : 11/886191  
DATED : June 11, 2013  
INVENTOR(S) : Dierker Page 1 of 1

It is certified that error appears in the above-identified patent and that said Letters Patent is hereby corrected as shown below:

In the Claims

Claim 7, column 4, line 33, change the claim dependency from "5" to -- "6" --.

Signed and Sealed this  
Twenty-ninth Day of April, 2014

Michelle K. Lee  
*Deputy Director of the United States Patent and Trademark Office*